United States Patent
Ashizuka (10) Patent No.: US 12,414,680 B2
(45) Date of Patent: Sep. 16, 2025

(54) ENDOSCOPE AND SUCTION-TARGET-OBJECT SUCTION METHOD

(71) Applicant: OLYMPUS MEDICAL SYSTEMS CORP., Tokyo (JP)

(72) Inventor: Masahiro Ashizuka, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 383 days.

(21) Appl. No.: 18/102,892

(22) Filed: Jan. 30, 2023

(65) Prior Publication Data

US 2023/0248227 A1 Aug. 10, 2023

Related U.S. Application Data (60) Provisional application No. 63/307,707, filed on Feb. 8, 2022.

(51) Int. Cl.
*A61B 1/00* (2006.01)
*A61B 1/015* (2006.01)

(52) U.S. Cl.
CPC .......... *A61B 1/015* (2013.01); *A61B 1/00039* (2013.01); *A61B 1/00094* (2013.01)

(58) Field of Classification Search
CPC .. A61B 1/015; A61B 1/00039; A61B 1/00094
See application file for complete search history.

(56) References Cited

U.S. PATENT DOCUMENTS

| | | | | |
|---|---|---|---|---|
| 5,503,616 A | * | 4/1996 | Jones | A61B 1/00135 600/156 |
| 2006/0235458 A1 | * | 10/2006 | Belson | A61M 25/0032 606/191 |
| 2015/0196735 A1 | | 7/2015 | Olig et al. | |
| 2019/0274887 A1 | * | 9/2019 | Godwin | A61B 1/00119 |

FOREIGN PATENT DOCUMENTS

| | | |
|---|---|---|
| JP | 2005-131163 A | 5/2005 |
| JP | 2016-140574 A | 8/2016 |
| JP | 2017-504411 A | 2/2017 |

* cited by examiner

*Primary Examiner* — Timothy J Neal
(74) *Attorney, Agent, or Firm* — Morgan, Lewis & Bockius LLP

(57) ABSTRACT

An insertion device includes an insertion portion having an outer peripheral surface and configured to be inserted into a subject, and a suction pipeline provided on the outer peripheral surface of the insertion portion. The suction pipeline is switchable from a first state to a second state and the suction pipeline is configured to maintain the second state. In the first state, a distal end of the suction pipeline is folded, and in the second state, the distal end of the suction pipeline is unfolded.

19 Claims, 5 Drawing Sheets

ENDOSCOPE AND SUCTION-TARGET-OBJECT SUCTION METHOD

RELATED APPLICATION DATA

This application is based on and claims priority under 35 U.S.C. § 119 to U.S. Provisional Application No. 63/307,707 filed on Feb. 8, 2022, the entire contents of which are incorporated herein by reference.

FIELD OF THE DISCLOSURE

The present disclosure relates to an endoscope provided with a suction pipeline on an outer periphery of an insertion portion, and a suction method of suctioning a suction target object by using the endoscope.

BACKGROUND

Conventionally, treatment performed on a living body tissue by using an endoscope inserted into a body cavity has been performed by using a treatment instrument inserted into a treatment instrument insertion channel inserted and disposed in an insertion portion of the endoscope. Examples of specific treatment include resection treatment of a target living body tissue, and stanching treatment of a target bleeding place.

A conventional endoscope has a function to suction and remove, for example, blood or residuum (including solidified materials; hereinafter referred to as a suction target object) due to bleeding or the like from a treatment target site or vicinity of the treatment target site. In this case, a treatment instrument insertion channel of the endoscope is sometimes used as a suction pipeline.

It may be requested to use a treatment instrument having a diameter larger than an inner diameter of the treatment instrument insertion channel provided in the conventional endoscope. In a case of heavy bleeding, emergency bleeding, or the like, suction performance may be insufficient only with the suction function using the treatment instrument insertion channel provided in the endoscope.

Japanese Patent Application Laid-Open Publication No. 2005-131163 and other documents have presented various disclosures of an external channel device that allows the use of a treatment instrument having a diameter larger than the inner diameter of the treatment instrument insertion channel provided in the endoscope or has suction performance higher than suction performance of the suction function using the treatment instrument insertion channel provided in the endoscope.

The external channel device disclosed by Japanese Patent Application Laid-Open Publication No. 2005-131163 and other documents includes a flexible tube formed to be able to be attached to and detached from an endoscope insertion portion, and a mantle portion that covers a distal end of the flexible tube. A communication hole that communicates with the flexible tube is formed at the mantle portion. The communication hole has an opening area larger than opening area of a distal end opening of the flexible tube. The flexible tube is fixed on an outer peripheral surface of the endoscope by using a medical tape.

With such a configuration, the distal end of the flexible tube is covered by the mantle portion in an endoscope provided with the conventional external channel device disclosed in the above-described publication and documents.

SUMMARY OF THE DISCLOSURE

An insertion device according to an aspect of the present disclosure includes an insertion portion having an outer peripheral surface and configured to be inserted into a subject, and a suction pipeline provided on the outer peripheral surface of the insertion portion. The suction pipeline is switchable from a first state to a second state and the suction pipeline is configured to maintain the second state. In the first state, a distal end of the suction pipeline is folded, and in the second state, the distal end of the suction pipeline is unfolded.

A method to suction an object using the insertion device includes applying pressure to an inner peripheral surface of a suction pipeline, switching the suction pipeline from a first state to the second state, and in the second state, suctioning an object from around an opening of the suction pipeline toward the opening of the suction pipeline and into an interior of the suction pipeline.

DETAILED DESCRIPTION

Typically, a conventional external channel device is fixed on an outer periphery side of an insertion portion of an endoscope. Thus, when fixed on the outer periphery side of the insertion portion of the endoscope, the external channel device partially protrudes outside an outer diameter of the endoscope.

Thus, when the insertion portion of the endoscope on which the conventional external channel device is mounted is inserted into a body cavity of a target subject of treatment, examination, or the like, operability of the endoscope on which the conventional external channel device is mounted potentially decreases as compared to operability of the endoscope without the external channel device. Accordingly, improvement of operability of the endoscope on which the external channel device is mounted has been constantly requested. For example, it is a problem that work is needed to remove the external channel device from the endoscope on which the external channel device is mounted when a medical tape is used to fix the external channel device to an outer periphery of the insertion portion of the endoscope.

According to an embodiment of the present disclosure described below, it is possible to contribute to improving insertion operability of an endoscope on an outer periphery of which a suction pipeline is mounted, and it is also possible to easily remove the suction pipeline from the endoscope after use of the suction pipeline. Thus, it is possible to provide an endoscope that can contribute to reducing an operation load on a user.

The present disclosure will be described below with reference to an illustrated embodiment. Note that each drawing used in the description below is schematically illustrated, and a dimensional relation among members, a scale, and the like are illustrated differently for each constituent component in some cases to illustrate the constituent component in a size with which the constituent component is recognizable on the drawing. Thus, the present disclosure is not limited to an illustrated form as for the number, shape, size ratio, relative positional relation, and the like of each constituent component illustrated in each drawing.

Figure 1:
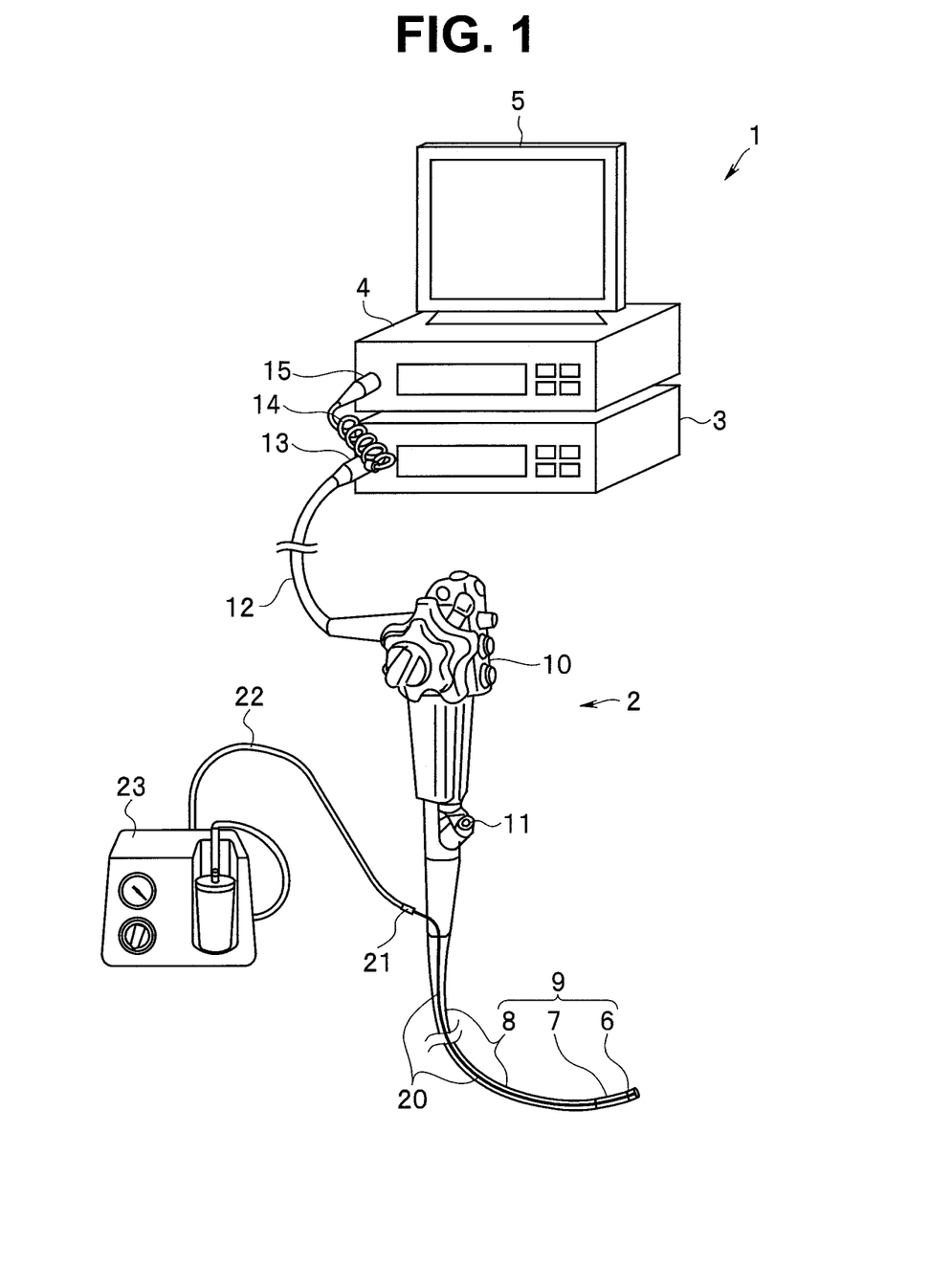
FIG. 1 is a schematic configuration diagram of an endoscope system including an endoscope according to an embodiment of the present disclosure.
Figure 2:
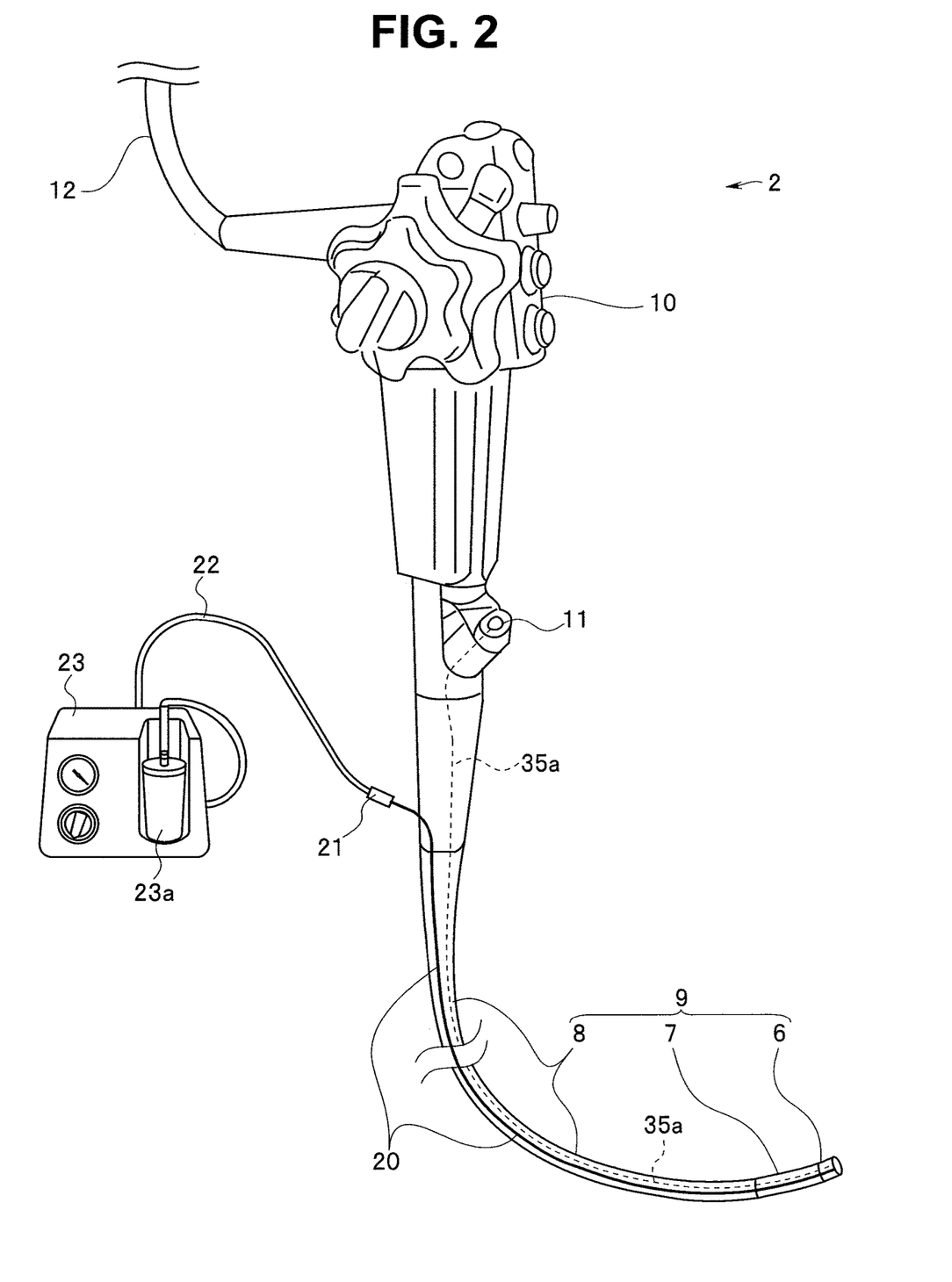
FIG. 2 is a schematic configuration diagram of the endoscope and a suction device according to the embodiment of the present disclosure.
Figure 3:
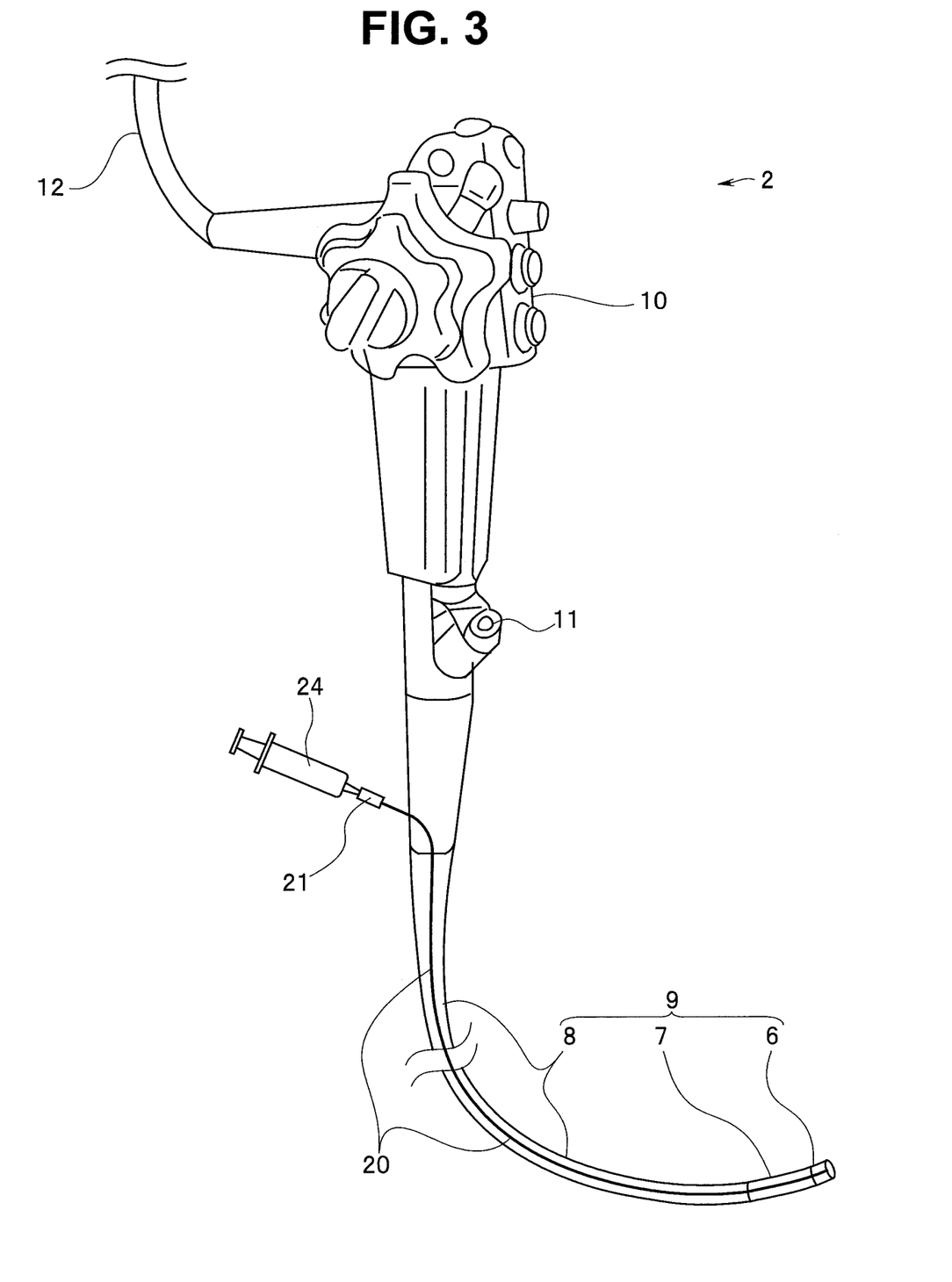
FIG. 3 is a schematic diagram illustrating an action when a suction pipeline of the endoscope according to the embodiment of the present disclosure is expanded.

First, configurations of an endoscope according to an embodiment of the present disclosure and an endoscope system including the endoscope will be described below with reference to FIGS. 1 and 2. FIG. 1 is a schematic configuration diagram of the endoscope system including the endoscope according to the embodiment of the present disclosure. FIG. 2 is a schematic configuration diagram of the endoscope and a suction device according to the embodiment of the present disclosure. Note that FIG. 3 is a schematic view illustrating an action when a suction pipeline of the endoscope according to the embodiment of the present disclosure is expanded.

An endoscope system 1 illustrated in FIG. 1 has the basic configuration as a conventional endoscope system. Thus, the description below is schematically made on each constituent member in the endoscope system 1.

The endoscope system 1 including an endoscope 2 according to the present embodiment is constituted by the endoscope 2, a light source device 3, a video processor 4, a display device 5, and the like.

The endoscope 2 is mainly constituted by an insertion portion 9 having an elongated pipe shape, the insertion portion 9 is extended from an operation portion 10, a universal cord 12, a suction pipeline 20 provided on an outer periphery of the insertion portion 9, and a suction device 23.

The insertion portion 9 is constituted by a distal end portion 6, a bending portion 7, and a flexible tube portion 8, which are provided continuously and sequentially from a distal end side. A proximal end portion of the insertion portion 9 is connected to the operation portion 10. Although described later in detail, the suction pipeline 20 is provided on an outer surface of the distal end portion 6. The insertion portion 9 has an outer peripheral surface and is configured to be inserted into the target subject. The suction pipeline 20 is provided on the outer peripheral surface of the insertion portion 9.

An image pickup unit, an illumination unit, and the like, which are not illustrated, are provided inside the distal end portion 6. Note that the distal end portion 6 has the internal configuration as a conventional endoscope. Thus, details of the internal configuration are neither illustrated nor described (refer to FIGS. 4 and 5 to be described later).

The operation portion 10 includes a forceps port 11 having an opening for inserting a non-illustrated treatment instrument or the like, an operation portion body serving as a grasping portion, and a plurality of operation members that are provided on an outer surface of the operation portion body and with which various operations of the endoscope 2 are performed.

The forceps port 11 provided at the operation portion 10 is a proximal end opening of a treatment-instrument-insertion-channel suction pipeline 35a (refer to FIG. 2) inserted and disposed between the operation portion 10 and a distal end opening (refer to reference sign 35 in FIGS. 4 and 5 to be described later) of the distal end portion 6 of the insertion portion 9.

The universal cord 12 is a cylindrical member extending from a side of the operation portion 10. A scope connector 13 is provided at a distal end of the universal cord 12. The scope connector 13 is connected to the light source device 3.

The light source device 3 is a device configured to supply illumination light to an illumination optical system or illumination apparatus (not illustrated) provided inside the distal end portion 6 of the insertion portion 9 of the endoscope 2. The illumination light emitted from the light source device 3 is transferred from the light source device 3 to the distal end portion 6 of the insertion portion 9 of the endoscope 2 through an optical fiber cable or the like (not illustrated) inserted and disposed in the scope connector 13, the universal cord 12, the operation portion 10, and the insertion portion 9. Then, the illumination light is transmitted through an illumination optical member (reference sign 32 in FIGS. 4 and 5 to be described later) provided on a front surface of the distal end portion 6, and is emitted toward an observation target object on a front side of the distal end portion 6.

Note that, in the exemplary description above, the illumination apparatus has a configuration in which the illumination light from the light source device 3 is transferred to the distal end portion 6 through the optical fiber cable or the like, but is not limited to the configuration. For example, an LED as an illumination light source may be provided inside the distal end portion 6, and light emission from the illumination light source (LED) may be controlled by the light source device 3.

A scope cable 14 extends toward a side from the scope connector 13. An electric connector portion 15 is provided at a distal end of the scope cable 14. The electric connector portion 15 is connected to the video processor 4.

The video processor 4 is a control device configured to control the entire endoscope system 1. In this case, the video processor 4 includes a signal processing circuit, a control processing circuit and the like, the signal processing circuit being configured to perform predetermined signal processing upon reception of an image pickup signal from the image pickup unit (not illustrated) provided inside the distal end portion 6 of the insertion portion 9 of the endoscope 2, the control processing circuit being configured to output a control signal for driving the image pickup unit and the like.

The video processor 4 and the image pickup unit are electrically connected to each other through a signal transmission cable (not illustrated). Thus, the signal transmission cable is inserted and disposed in the electric connector portion 15, the universal cord 12, the operation portion 10, and the distal end portion 6 of the insertion portion 9. With this configuration, an image pickup signal outputted from the image pickup unit, a control signal outputted from the video processor 4, and the like are transferred between the image pickup unit and the video processor 4 through the signal transmission cable. Note that the signal transmission cable is, for example, a composite cable as a plurality of cables bundled and covered by an external skin shield, an external skin tube, or the like.

The video processor 4 and the display device 5 are connected to each other through a video cable (not illustrated). The video cable transmits, to the display device 5, an image signal, a control signal, and the like outputted from the video processor 4.

The display device 5 receives an image signal and a control signal outputted from the video processor 4 and displays an endoscope image and various kinds of information in a predetermined display form in accordance with the received control signal.

The endoscope 2 according to the present embodiment includes the suction pipeline 20 in a predetermined form in a long axis direction on the outer periphery of the insertion portion 9. The suction pipeline 20 is provided on the outer periphery between the distal end portion 6 of the insertion portion 9 and the proximal end portion of the insertion portion 9. A coupling member 21 is provided at a proximal end of the suction pipeline 20. The coupling member 21 is a member for coupling a distal end of a suction tube 22 extended from the suction device 23 to be described later, or a tube end of a gas-liquid feeding syringe 24 to be described later.

The suction tube 22 or the gas-liquid feeding syringe 24 is coupled to the coupling member 21 as appropriate and necessary when the endoscope 2 is used. A proximal end of the suction tube 22 is connected to the suction device 23.

The suction device 23 is a device configured to suction mucus, bleeding, residuum, and the like, which would cause failure of observation in a body cavity, in combination with the endoscope 2. The proximal end of the suction tube 22 is coupled to the suction device 23. The distal end of the suction tube 22 is connected to the coupling member 21 when the suction device 23 is used. With this configuration, the suction device 23 can suction mucus, bleeding, residuum, and the like in the body cavity through the suction tube 22 and the suction pipeline 20. Note that the suction device 23 is a typical device practically used in conventional cases. Thus, configurations and effects of the suction device 23 are not described in detail.

Figure 4:
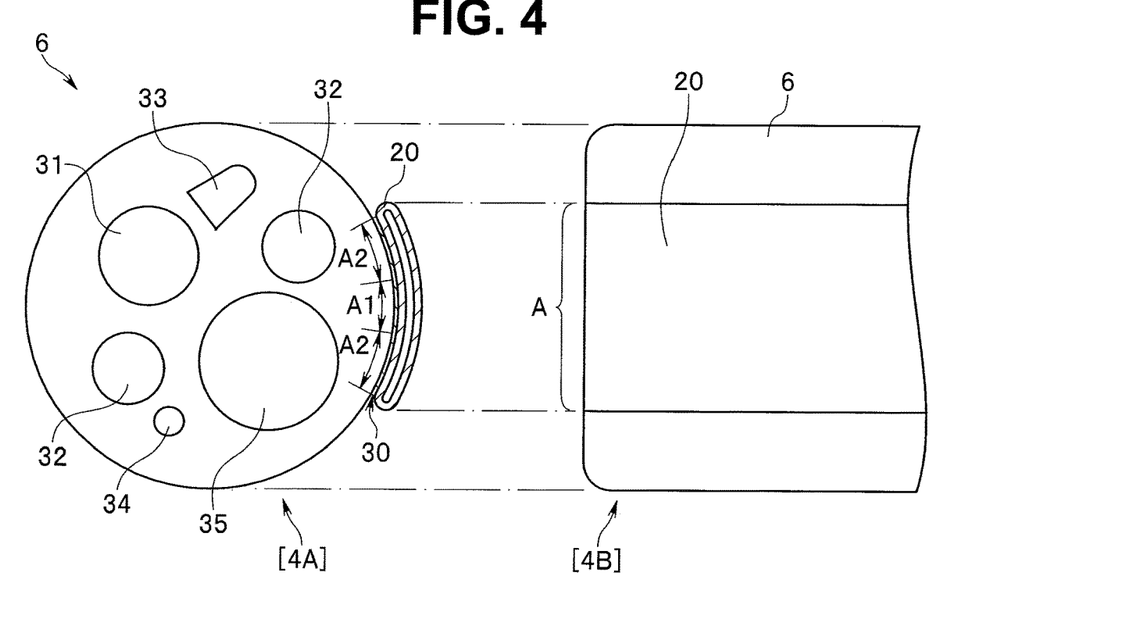
FIG. 4 is a plan view illustrating a front surface of a distal end portion of the endoscope according to the embodiment of the present disclosure and a plan view illustrating part of a side surface of the distal end portion (when no load is applied to the suction pipeline).
Figure 5:
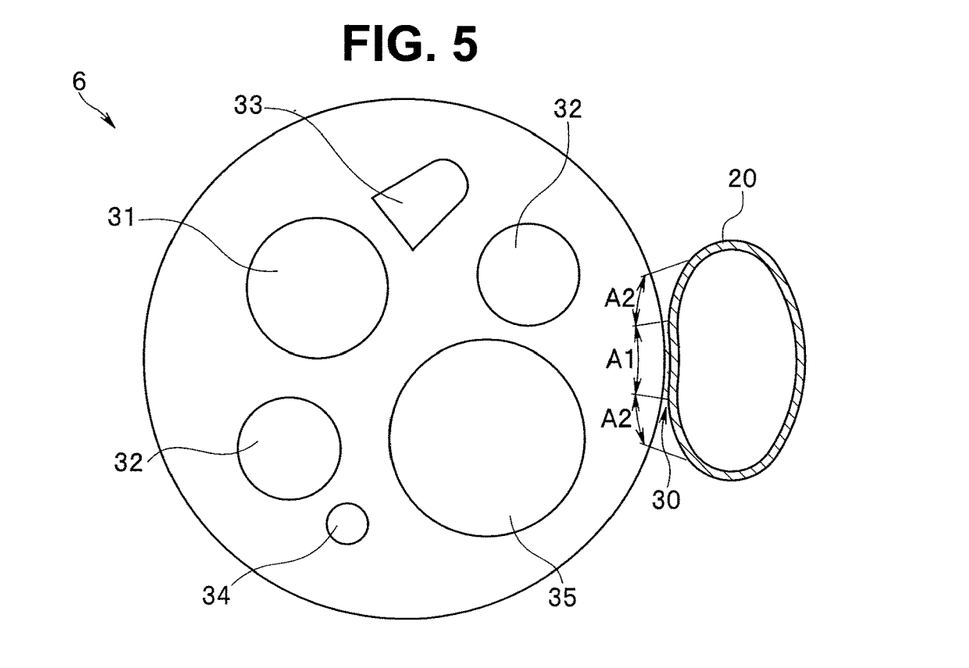
FIG. 5 is an enlarged plan view illustrating the front surface of the distal end portion of the endoscope according to the embodiment of the present disclosure (when a load is applied to the suction pipeline).

Subsequently, a detailed configuration of the suction pipeline 20 provided in the endoscope 2 according to the present embodiment will be described below with reference to FIGS. 4 and 5. FIGS. 4 and 5 are diagrams illustrating a simplified configuration of the distal end portion of the endoscope according to the embodiment of the present disclosure. FIG. 4 is a plan view (reference sign [4A]) illustrating the front surface of the distal end portion of the endoscope and a plan view (reference sign [4B]) illustrating part of a side surface of the distal end portion. Similarly to reference sign [4A] in FIG. 4, FIG. 5 is an enlarged plan view of the front surface of the distal end portion of the endoscope. In this case, FIG. 4 illustrates a non-load state in which no load such as pressure due to gas, liquid, or a suction target object is applied to the suction pipeline. FIG. 5 illustrates a state in which a load is applied to the suction pipeline. Note that sections of the suction pipeline are illustrated in FIGS. 4 and 5. The suction pipeline 20 is switchable from a first state to a second state and the suction pipeline is configured to maintain the second state. In the first state, a distal end of the suction pipeline 20 may be folded or may have a reduced diameter at the distal end. In the second state, the distal end of the suction pipeline 20 may be unfolded or may have increased diameter at a distal end. The suction pipeline 20 is switchable from the first state to the second state when pressure is applied to an inside of the suction pipeline 20. The suction pipeline 20 may maintain the second state in the presence or absence of some input or application of pressure. The suction pipeline 20 may be irreversibly switchable from the first state to the second state. Once in the second state, the suction pipeline 20 may stay in the second state.

As illustrated, an observation window 31, (two) illumination windows 32, a gas-liquid feeding nozzle 33, an auxiliary liquid feeding port 34, a treatment-instrument-insertion-channel suction opening 35, and the like are provided on a distal end surface of the distal end portion 6 of the insertion portion 9 of the endoscope 2 according to the present embodiment.

The observation window 31 is an optically transparent optical member serving as part of an observation optical system. The observation optical system is a constituent member having a function to image an optical image of an observation target object. The image pickup unit including an image pickup device, a drive circuit of the image pickup device, a signal processing circuit and the like is disposed on a back side of the observation optical system.

The illumination windows 32 are optically transparent optical members serving as part of the illumination optical system or the illumination apparatus. The illumination windows 32 are a constituent member having a function to emit a light beam transferred from the light source device 3 toward an observation target object on the front side of the distal end portion 6 as described above. Note that, in the endoscope 2 according to the present embodiment, the illumination windows 32 may be provided at opposite positions, respectively, through the observation window 31.

The gas-liquid feeding nozzle 33 is a constituent member having a function to eject or spray gas or liquid toward a front surface of the observation window 31 or the illumination windows 32 to remove mucus, bleeding, or the like that adheres to the front surface of the observation window 31 or the illumination windows 32 and would cause observation failure.

The auxiliary liquid feeding port 34 is an opening through which liquid (water) for cleaning an affected part or the like is discharged. The auxiliary liquid feeding port 34 is a distal end opening of an auxiliary liquid feeding channel (not illustrated) inserted in the scope connector 13, the universal cord 12, the operation portion 10, and the insertion portion 9.

The suction pipeline 20 provided in the endoscope 2 according to the present embodiment is a cylindrical member formed in a cylinder as a whole. The suction pipeline 20 is formed in a state in which the diameter of at least a distal end opening is reduced (in other words, the opening is deformed flat and closed) when no load is applied (refer to FIG. 4). With such a form, it is possible to improve insertion easiness of the insertion portion 9. The state in which the diameter of the distal end opening is reduced is not limited to a state in which opposite sides of an inner peripheral surface of the distal end opening are completely in close contact with each other, but also a state in which a gap exists between opposite sides of the inner peripheral surface. When the distal end of the suction pipeline 20 is folded, at least a portion of an interior wall of the distal end of the suction pipeline 20 contact each other.

In a state in which a load such as pressure due to insertion of gas, liquid, a suction target object, or the like is applied to the inside of the suction pipeline 20 (refer to FIG. 5), the suction pipeline 20 may be deformed in a diameter increase direction into a cylindrical shape as a whole. In this case, the suction pipeline 20 forms a pipeline having a predetermined cross-sectional area. In this state, the suction pipeline 20 is maintained in a predetermined shape (for example, a cylindrical shape) due to rigidity or elastic force of the suction pipeline 20. This shape is maintained while suction is performed through the suction pipeline 20 in this state. In the second state, a fluid supplied to the suction pipeline 20 causes the interior wall of the distal end of the suction pipeline 20 to be not in contact with each other. The suction pipeline 20 may be sealed at a plurality of places intermittently along a length of the suction pipeline 20. In the first state, the suction pipeline may be folded over an entire length of the insertion portion. When the distal end of the suction pipeline 20 is unfolded, no portion of interior walls of the distal end of the suction pipeline 20 contact each other.

When the endoscope 2 according to the present embodiment is in an unused state (for example, a state at factory shipment), the suction pipeline 20 is provided in the long axis direction on the outer periphery of the insertion portion 9 as illustrated in FIG. 4. Details of a form of the suction pipeline 20 in this case are as follows.

Specifically, the suction pipeline 20 provided in the long axis direction on the outer periphery of the insertion portion 9 is maintained in a distal-end-opening closed state with flat deformation. In this case, a flat state of the suction pipeline 20 is a state in which the suction pipeline 20 is in the distal-end-opening closed state with deformation and opposite sides of the inner peripheral surface are in close contact with each other (state with no gap).

To maintain such a state of the suction pipeline 20, for example, opposite sides of the inner peripheral surface of the suction pipeline 20 are bonded to each other by using a living-body suitable bonding agent or the like having predetermined bonding force (not illustrated). In this case, the bonding of the opposite sides of the inner peripheral surface is achieved by relatively weak bonding force with which the bonding of the inner peripheral surface can be easily released by performing gas feeding or liquid feeding at predetermined pressure from a proximal end side of the suction pipeline 20. Note that the bonding of the opposite sides of the inner peripheral surface of the suction pipeline 20 may be achieved by thermal welding in place of the above-described living-body suitable bonding agent or the like.

The opposite sides of the inner peripheral surface may be bonded over an entire length of the suction pipeline 20 or may be bonded at a plurality of places at a predetermined interval. Alternatively, at least the distal end opening may be bonded into a reduced diameter state. In this case, the closed state of the entire pipeline can be maintained by applying suction to the suction pipeline 20 at use.

Note that the flat state of the suction pipeline 20 before the endoscope 2 is used is not limited to the above-described form. The suction pipeline 20 can have the distal-end-opening closed state with flat deformation, in other words, the reduced diameter state and may have, for example, a state in which opposite sides of the inner peripheral surface are not completely in close contact with each other but have a gap therebetween.

As illustrated in FIG. 4, part of an outer surface of the suction pipeline 20 in such a form is bonded to part of the outer periphery of the insertion portion 9 by using a living-body suitable bonding agent or the like 30. The part of the outer surface of the suction pipeline 20 corresponds to regions denoted by reference signs A1 and A2 in a diagram denoted by reference sign [4A] in FIG. 4. The part of the outer periphery of (the distal end portion 6 of) the insertion portion 9 of the endoscope 2 corresponds to a range denoted by reference sign A in a diagram denoted by reference sign [4B] in FIG. 4.

In this case, the partial region A of the outer periphery of the insertion portion 9 and the partial region (A1 and A2) of the outer surface of the suction pipeline 20 are bonded to each other over the entire length of the insertion portion 9 from a distal end to a proximal end. Alternatively, the bonding may be provided at a plurality of places at a predetermined interval between the distal end and proximal end of the insertion portion 9.

Note that the outer periphery of the insertion portion 9 and the suction pipeline 20 may be bonded to each other by thermal welding in place of the living-body suitable bonding agent or the like 30. In this case, the bonding is provided in appropriate strength with which the bonding can be easily removed after the suction pipeline 20 is used.

Moreover, the bonding of the outer periphery of the insertion portion 9 and the suction pipeline 20 is configured as follows. Specifically, as described later, a load such as pressure is applied inside the suction pipeline 20 through gas, liquid, a suction target object, or the like when the suction pipeline 20 is used (refer to FIG. 5). In this case, the suction pipeline 20 deforms in the diameter increase direction into a cylindrical shape as a whole. In this state, the bonding of the suction pipeline 20 is easily released in partial regions (denoted by reference sign A2) closer to respective outer edges in a circumferential direction among the bonding regions A1 and A2 on the outer periphery of the insertion portion 9. With this configuration, the suction pipeline 20 easily deforms in the diameter increase direction. The suction pipeline 20 includes a wall having a first outer surface portion facing toward the insertion portion 9. The first outer surface portion includes a first area section A1 and a second area section A2. In the first state, the first area section A1 is bonded to the outer peripheral surface of the insertion portion 9 and the second area section A2 is bonded to the outer peripheral surface of the insertion portion 9. In the second state, the first area section A1 does not contact the outer peripheral surface of the insertion portion 9 and the second area section A2 is bonded to the outer peripheral surface of the insertion portion 9. In the first state, portions of an inner peripheral surface of the suction pipeline 20 are bonded to each other by a third bonding force to seal the suction pipeline 20, and the third bonding force is lower than the second bonding force.

In this case, the bonding is maintained in a partial region (denoted by reference sign A1) at a center in the circumferential direction among the bonding regions A1 and A2 of the suction pipeline 20 and the outer periphery of the insertion portion 9. With this configuration, the suction pipeline 20 in an increased diameter state does not fall off the outer periphery of the insertion portion 9. Thus, it is possible to perform a suction operation without interference.

In the endoscope 2 according to the present embodiment, bonding force in each region (bonding region A2) on an outer edge side among the partial region A of the outer periphery of the insertion portion 9 and the bonding regions A1 and A2 on the suction pipeline 20 is weaker than bonding force in the partial region (bonding region A1) at the center (A1>A2). The first area section A1 and the outer peripheral surface of the insertion portion 9 are bonded by a first bonding force. The second area section A2 and the outer peripheral surface of the insertion portion 9 are bonded by second bonding force. The first bonding force is lower than the second bonding force.

In this case, the bonding force in each region (bonding region A2) on an outer edge side among the partial region A of the outer periphery of the insertion portion 9 and the bonding regions A1 and A2 on the suction pipeline 20 is stronger than bonding force between opposite sides of the inner peripheral surface of the suction pipeline 20. Thus, when the bonding force on the opposite sides of the inner surface of the suction pipeline 20 is denoted by reference sign B, a relation among the bonding forces is as follows:

$$A1 > A2 > B.$$

With this configuration, when a load such as pressure is applied inside the suction pipeline 20 to increase the diameter at use of the suction pipeline 20, bonding B of the opposite sides of the inner surface is released first, and then bonding in each bonding region A2 is released. In this case, bonding is maintained in the bonding region A1.

Then, after use, the suction pipeline 20 can be removed by releasing bonding in the bonding region A1.

The endoscope system 1 including the endoscope 2 according to the present embodiment is configured as schematically described above.

The following describes an action (suction method) when a suction target object is suctioned by using the endoscope 2 according to the present embodiment thus configured. The method to suction an object using the insertion device includes applying pressure to an inner peripheral surface of the suction pipeline, switching the suction pipeline from the first state to the second state, and in the second state, suctioning an object from around an opening of the suction pipeline toward the opening of the suction pipeline and into an interior of the suction pipeline. The method may include attaching the suction pipeline on the outer peripheral surface of the insertion portion by bonding. The insertion portion may be a part of an endoscope.

In the endoscope 2 according to the present embodiment, the suction pipeline 20 is provided on the outer periphery of the insertion portion 9. The suction pipeline 20 has a reduced diameter at least at a distal end. An outer periphery of the suction pipeline 20 is bonded along an outer peripheral surface of the insertion portion 9, and opposite sides of the inner surface of the suction pipeline 20 are bonded to each other, and accordingly, the suction pipeline 20 has a shape along the outer periphery of the insertion portion 9. In this manner, a distal end opening of the suction pipeline 20 is closed. The applying pressure includes supplying a fluid to the interior of the suction pipeline.

The insertion portion 9 of the endoscope 2 on which the suction pipeline 20 is mounted as described above is inserted into a body cavity of a treatment or examination target subject in accordance with a normal endoscope insertion operation. Then, when the distal end portion 6 of the insertion portion 9 has reached a treatment or examination target site, the gas-liquid feeding syringe 24 is coupled to the coupling member 21 on a hand side of the endoscope 2, in other words, the proximal end of the suction pipeline 20 (refer to FIG. 3).

Then, pressure is applied in the suction pipeline 20 by using the gas-liquid feeding syringe 24. The pressure releases the bonding between opposite sides of the inner peripheral surface of the suction pipeline 20. Simultaneously, bonding in each bonding region A2 among the bonding regions on the suction pipeline 20 and the part of the outer periphery of the insertion portion 9 is released. In this manner, when the suction pipeline 20 is expanded (the diameter is increased to an opened state), the distal end opening becomes an opened state. The opened state of the suction pipeline 20 is maintained even when the pressure from the gas-liquid feeding syringe 24 is released.

Subsequently, the gas-liquid feeding syringe 24 is removed from the coupling member 21 at the proximal end of the suction pipeline 20. Then, the distal end of the suction tube 22 of the suction device 23 is connected to the coupling member 21 of the proximal end of the suction pipeline 20 as illustrated in FIGS. 1 and 2. Thereafter, the suction device 23 is actuated. Accordingly, a suction target object (mucus, bleeding, residuum or the like in the body cavity) around the distal end opening of the suction pipeline 20 is suctioned from the distal end opening of the suction pipeline 20 to the hand side (the suction device 23 side) through the suction pipeline 20. The suction target object thus suctioned is accumulated from the suction pipeline 20 into a suction bottle 23a (refer to FIG. 2) of the suction device 23 through the suction tube 22.

After the suction pipeline 20 is used in this manner, the endoscope 2 is removed out of the body cavity of the subject. Then, the suction pipeline 20 is removed from the outer periphery of the insertion portion 9 of the endoscope 2. Thereafter, the endoscope 2 from which the suction pipeline 20 is removed can be inserted into the body cavity of the subject again as necessary and used for a procedure.

As described above, according to the embodiment, the distal end of the suction pipeline 20 provided in the long axis direction on the outer periphery of the insertion portion 9, which is elongated and inserted into a subject, has a reduced diameter before use. Accordingly, the suction pipeline 20 is closed at insertion of the insertion portion 9 into the subject, and thus does not interfere with insertion of the insertion portion 9 even when the suction pipeline 20 is mounted on the outer periphery of the insertion portion 9.

Accordingly, a smooth insertion operation can be constantly ensured with the endoscope according to the present embodiment. Thus, with a configuration according to the present embodiment, it is possible to contribute to improving insertion operability of the endoscope 2 in which the suction pipeline 20 is provided on the outer periphery of the insertion portion 9.

When the suction pipeline 20 is used after the insertion portion 9 is inserted into a subject, the distal end opening is expanded by applying pressure from the hand side to the suction pipeline 20. Accordingly, the suction pipeline 20 can be used as a suction pipeline having a diameter larger than a diameter of the treatment-instrument-insertion-channel suction pipeline 35a provided in the endoscope 2. The suction pipeline in the second state has a first inner diameter, treatment-instrument-insertion-channel suction pipeline 35a includes a treatment insertion channel having a second inner diameter. The first inner diameter is larger than the second inner diameter.

Moreover, after the suction pipeline 20 is used, the suction pipeline 20 can be easily removed from the outer periphery of the insertion portion 9 of the endoscope 2 after removed from a body cavity of the subject. Accordingly, it is possible to contribute to reducing an operation load on a user.

Subsequently, a modification of the suction pipeline in the endoscope according to the above-described embodiment will be described below with reference to FIGS. 6 and 7.

A suction pipeline 20A according to the present modification may be basically the same as in the above-described embodiment. Only difference is that elastic bodies (25a and 25b) in predetermined forms are provided on an inner peripheral surface of the suction pipeline 20A according to the present modification. Thus, any component the same as in the above-described embodiment is denoted by the same reference sign and detailed description of the component is omitted, and only difference will be described below in detail.

Figure 6:
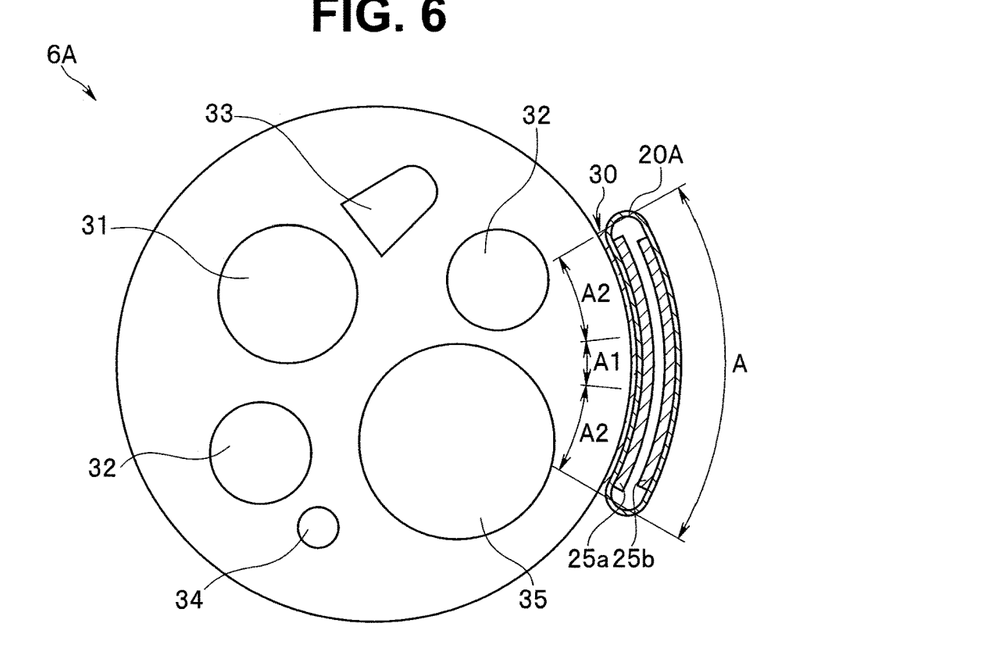
FIG. 6 is a plan view corresponding to a modification of the suction pipeline in the endoscope according to the embodiment of the present disclosure and illustrating the front surface of the distal end portion of the endoscope (when no load is applied to the suction pipeline).
Figure 7:
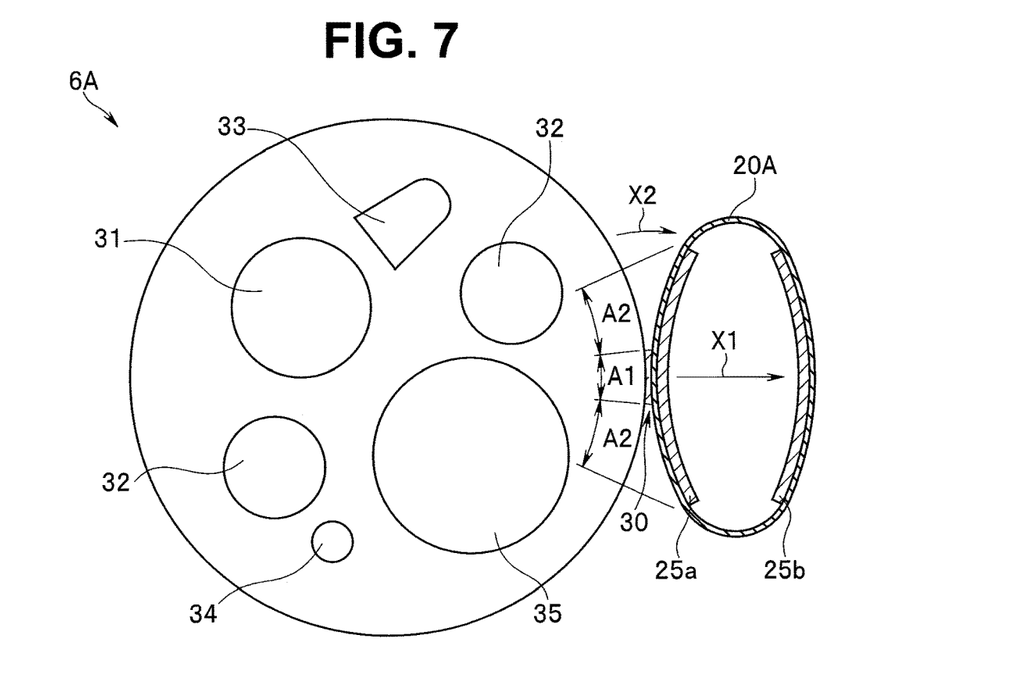
FIG. 7 is a plan view corresponding to the modification of the suction pipeline in the endoscope according to the embodiment of the present disclosure and illustrating the front surface of the distal end portion of the endoscope (when a load is applied to the suction pipeline).

FIGS. 6 and 7 are plan views corresponding to the modification of the suction pipeline in the endoscope according to the embodiment of the present disclosure and illustrating the front surface of the distal end portion of the endoscope. FIG. 6 illustrates no load is applied to the suction pipeline. FIG. 7 illustrates a state in which a load is applied to the suction pipeline. Note that sections of the suction pipeline are illustrated in FIGS. 6 and 7.

Similarly to the above-described embodiment, the suction pipeline 20A according to the present modification is provided between a distal end portion 6A of the insertion portion 9 and the proximal end portion of the insertion portion 9 in the long axis direction on the outer periphery of the insertion portion 9.

Similarly to the above-described embodiment, the suction pipeline 20A is a cylindrical member formed in a cylinder as a whole. In the suction pipeline 20A according to the present modification, for example, a pair of elastic bodies (25a and 25b) are provided on an inner peripheral surface at least at a distal end.

The pair of elastic bodies (25a and 25b) are each, for example, what is called a plate spring made of a thin plate having an arc shape. In this case, a constituent material of the pair of elastic bodies (25a and 25b) is, for example, a metallic material (such as stainless steel) or a resin material.

Specifically, the pair of elastic bodies (25a and 25b) are a first elastic body 25a disposed at a position closer to the outer peripheral surface of the insertion portion 9 (inner position in the pipeline) in a state in which the suction pipeline 20A is mounted on the insertion portion 9, and a second elastic body 25b disposed on an outer periphery side of the first elastic body 25a (at an outer position in the pipeline) when the suction pipeline 20A is in the state, the second elastic body 25b being disposed at a position opposite to the first elastic body 25a. In the first state, the elastic bodies (25a and 25b) bias the suction pipeline 20 to be folded, and the elastic bodies (25a and 25b) extend along the outer peripheral surface of the insertion portion 9. In the second state, the elastic bodies (25a and 25b) bias the suction pipeline 20 to be opened.

The pair of elastic bodies (25a and 25b) each have an arc shape as illustrated in FIG. 7 in a state (normal state) in which no load is applied. In this case, as illustrated in FIG. 7, the first elastic body 25a is disposed with an arc in a direction departing from an outer peripheral shape (arc shape) of the insertion portion 9. The second elastic body 25b is disposed with an arc along the outer peripheral shape (arc shape) of the insertion portion 9.

Accordingly, a distal end opening is formed by the shapes of the pair of elastic bodies (25a and 25b) and maintained in a state (state in FIG. 7) in which a load is applied to the suction pipeline 20A. In this case, the state of the first elastic body 25a is referred to as a second state in which the suction pipeline 20A has an increased diameter at a distal end.

In a state (state in FIG. 6) no load is applied to the suction pipeline 20A, part (the bonding regions A1 and A2 in FIG. 6) of an outer surface of the suction pipeline 20A is bonded to part of the outer periphery of the insertion portion 9 (refer to reference sign A in FIG. 6) by using the living-body suitable bonding agent or the like 30. In this case, the first elastic body 25a receives application of a load due to bonding force of the living-body suitable bonding agent or the like 30 and elastically deforms in a shape along the outer periphery of the insertion portion 9 as illustrated in FIG. 6. A state of the first elastic body 25a in this case is referred to as a first state in which the suction pipeline 20A has a reduced diameter at the distal end.

Note that, in this state (state in FIG. 6), opposite sides of inner peripheral surface are bonded to each other by using the living-body suitable bonding agent or the like at a part where the pair of elastic bodies (25a and 25b) are not disposed inside the suction pipeline 20A.

When a load is applied to the suction pipeline 20A in this state, the second elastic body 25b moves in an arrow X1 direction in FIG. 7, and simultaneously, bonding in the bonding region A2 starts being released (refer to arrow reference sign X2 in FIG. 7). Accordingly, the first elastic body 25a starts returning to the normal state illustrated in FIG. 7 by elastic restoring force of the first elastic body 25a. As a result, bonding in the bonding region A2 is released, and simultaneously, the first elastic body 25a transitions to the eventual state in FIG. 7.

To achieve such an action, it can have, in the bonding region A2, bonding force with which elastic deformation of the first elastic body 25a can be maintained against elastic force of the first elastic body 25a. In other words, the first elastic body 25a has elastic force weaker than bonding force of the living-body suitable bonding agent or the like 30 in the bonding region A2. The other configurations and effects of the present modification may be the same as configurations and effects of the above-described embodiment.

According to the above-described modification thus configured, it is possible to obtain the same effects as the effects of the above-described embodiment. Moreover, in the present modification, the pair of elastic bodies (25a and 25b) are provided at least at the distal end of the suction pipeline 20A. With this configuration, in a state in which a load is applied to the suction pipeline 20A, a distal end opening is formed by the pair of elastic bodies (25a and 25b) and reliably maintained while suction is performed by using the suction pipeline 20A. When no load is applied to the suction pipeline 20A, the suction pipeline 20A can be reliably disposed on the outer periphery of the insertion portion 9 in a state in which the distal end of the suction pipeline 20A is closed along the outer periphery of the insertion portion 9. Thus, it is possible to contribute to further improving operability of the insertion portion 9 of the endoscope 2 on which the suction pipeline 20A is mounted.

Note that the pair of elastic bodies (25a and 25b) in the suction pipeline 20A according to the above-described modification may be provided at least at a distal end part of the suction pipeline 20A. Thus, the present disclosure is not limited to an exemplary configuration in the above-described modification in which the pair of elastic bodies are provided only at the distal end of the suction pipeline 20A.

For example, another elastic body may be provided at a middle part of the suction pipeline 20A in addition to the pair of elastic bodies (25a and 25b) provided at the distal end of the suction pipeline 20A. Alternatively, a plurality of elastic bodies may be provided at a plurality of places at a predetermined interval between the distal end of the suction pipeline 20A and a proximal end of the suction pipeline 20A.

In the above-described modification, each elastic body is a plate spring having a thin plate shape, but the same effect can be obtained by changing a thickness of the suction pipeline instead. For example, the same effect can be obtained by increasing the thickness of the pipeline corresponding to a part where the pair of elastic bodies (25a and 25b) are disposed in the above-described modification The present disclosure is not limited to the above-described embodiment but may be modified and applied in various kinds of manners without departing from the gist of the disclosure. Moreover, the above-described embodiment includes disclosure at various kinds of stages, and various kinds of disclosure can be extracted by combining a plurality of disclosed components as appropriate. For example, when some components described in the above-described embodiment are deleted, a configuration in which the components are deleted can be extracted as an disclosure as long as the technical problem can be solved and the advantageous effects of the disclosure can be obtained. In addition, constituent components in different embodiments may be combined as appropriate. The present disclosure is limited by the accompanying claims but not constrained by a particular aspect.

Example 1. An endoscope comprising:
an insertion portion that is elongated and inserted into a subject; and
a suction pipeline provided in a long axis direction on an outer periphery of the insertion portion and having a reduced diameter at a distal end.

Example 2. The endoscope according to Example 1, wherein
the insertion portion includes a treatment-instrument-insertion-channel suction pipeline through which a treatment instrument is inserted and gas and liquid are suctioned, and
a diameter of the suction pipeline increases when pressure is applied to an inner periphery from a hand side, and an inner diameter of the suction pipeline when having the increased diameter is larger than an inner diameter of the treatment-instrument-insertion-channel suction pipeline.

Example 3. The endoscope according to Example 1, wherein the suction pipeline has a reduced diameter over an entire length.

Example 4. The endoscope according to Example 1, wherein opposite sides of an inner peripheral surface of the suction pipeline at the distal end are bonded to each other.

Example 5. The endoscope according to Example 4, wherein the bonding of opposites sides of the inner peripheral surface of the suction pipeline is released when predetermined pressure is applied from the hand side to the inner periphery of the suction pipeline.

Example 6. The endoscope according to Example 1, wherein opposite sides of an inner peripheral surface of the suction pipeline are bonded to each other at a plurality of places at a predetermined interval in the long axis direction.

Example 7. The endoscope according to Example 1, wherein opposite sides of an inner peripheral surface of the suction pipeline are bonded to each other over an entire length.

Example 8. The endoscope according to Example 1, wherein the suction pipeline has an elastic body at the distal end.

Example 9. The endoscope according to Example 8, wherein
the elastic body has elastic force in a radial direction of the suction pipeline, and
the elastic body deforms to a first state in which the diameter of the suction pipeline at the distal end is reduced and a second state in which the diameter of the suction pipeline at the distal end is increased.

Example 10. The endoscope according to Example 9, wherein the elastic body
maintains the second state when no load is applied, and deforms to the first state when a load is applied.

Example 11. The endoscope according to Example 1, wherein the suction pipeline is bonded to the outer periphery of the insertion portion.

Example 12. The endoscope according to Example 11, wherein the suction pipeline is bonded to the outer periphery of the insertion portion by weaker bonding force in an outer edge region than in a substantially central region in a region in which the suction pipeline is bonded to the outer periphery of the insertion portion.

Example 13. The endoscope according to Example 11, wherein
opposite sides of an inner peripheral surface of the suction pipeline are bonded to each other over an entire length, and
the suction pipeline is bonded to the outer periphery of the insertion portion by bonding force stronger than force of the bonding of the opposite sides of the inner peripheral surface of the suction pipeline.

Example 14. A suction-target-object suction method comprising:
forming an opening through a suction pipeline by applying pressure from a hand side to expand the suction pipeline, the suction pipeline being provided on an outer periphery of an insertion portion of an endoscope and having a reduced diameter at least at a distal end; and
suctioning a suction target object around the opening toward the hand side of the suction pipeline through the opening.

Example 15. A suction-target-object suction method comprising:
mounting a suction pipeline on an outer periphery of an insertion portion of an endoscope, the suction pipeline having a reduced diameter at least at a distal end,
inserting, into a subject, the insertion portion on which the suction pipeline is mounted;
opening the distal end by applying pressure from a hand side to expand the suction pipeline; and
suctioning a suction target object around the opening toward the hand side of the suction pipeline through the opening.

Example 16. The suction-target-object suction method according to Example 15, wherein the suction pipeline is mounted on the outer periphery of the insertion portion by bonding.

What is claimed is:
1. An insertion device, comprising:
an insertion portion having an outer peripheral surface and configured to be inserted into a subject; and
a suction pipeline provided on the outer peripheral surface of the insertion portion,
wherein the suction pipeline is switchable from a first state to a second state and the suction pipeline is configured to maintain the second state,
wherein in the first state, a distal end of the suction pipeline is folded, and in the second state, the distal end of the suction pipeline is unfolded,
wherein the suction pipeline includes a wall having a first outer surface portion facing toward the insertion portion,
wherein the first outer surface portion includes a first area section and a second area section, wherein, in the first state, the first area section is bonded to the outer peripheral surface of the insertion portion and the second area section is bonded to the outer peripheral surface of the insertion portion, and wherein, in the second state, the first area section does not contact the outer peripheral surface of the insertion portion and the second area section is bonded to the outer peripheral surface of the insertion portion.

2. The insertion device according to claim 1, wherein, when the distal end of the suction pipeline is folded, at least a portion of interior walls of the distal end of the suction pipeline contact each other.

3. The insertion device according to claim 2, wherein in the second state, a fluid supplied to the suction pipeline causes the interior walls of the distal end of the suction pipeline to be not in contact with each other.

4. The insertion device according to claim 2, wherein, in the first state, portions of an inner peripheral surface of the suction pipeline are bonded to each other to seal the suction pipeline at a plurality of places intermittently along a length of the suction pipeline.

5. The insertion device according to claim 1, wherein, when the distal end of the suction pipeline is unfolded, no portion of interior walls of the distal end of the suction pipeline contact each other.

6. The insertion device according to claim 1, wherein, when the distal end of the suction pipeline is folded, at least a portion of interior walls of the distal end of the suction pipeline contact each other, and wherein, when the distal end of the suction pipeline is unfolded, no portion of the interior walls of the distal end of the suction pipeline contact each other.

7. The insertion device according to claim 1, wherein the suction pipeline is switchable from the first state to the second state when pressure is applied to an inside of the suction pipeline.

8. The insertion device according to claim 1, wherein the suction pipeline in the second state has a first inner diameter, wherein the insertion portion includes a treatment insertion channel having a second inner diameter, and wherein the first inner diameter is larger than the second inner diameter.

9. The insertion device according to claim 1, wherein, in the first state, the suction pipeline is folded over an entire length of the insertion portion.

10. The insertion device according to claim 1, wherein the distal end of the suction pipeline is an elastic body.

11. The insertion device according to claim 10, wherein, in the first state, the elastic body biases the suction pipeline to be folded.

12. The insertion device according to claim 10, wherein, in the second state, the elastic body biases the suction pipeline to be opened.

13. The insertion device according to claim 10, wherein, in the first state, the elastic body extends along the outer peripheral surface of the insertion portion.

14. The insertion device according to claim 1, wherein the first area section and the outer peripheral surface of the insertion portion are bonded by a first bonding force, wherein the second area section and the outer peripheral surface of the insertion portion are bonded by a second bonding force, and wherein the first bonding force is lower than the second bonding force.

15. The insertion device according to claim 14, wherein, in the first state, portions of an inner peripheral surface of the suction pipeline are bonded to each other by a third bonding force to seal the suction pipeline, and wherein the third bonding force is lower than the second bonding force.

16. A method to suction an object using the insertion device according to claim 1, comprising:

applying pressure to an inner peripheral surface of the suction pipeline;

switching the suction pipeline from the first state to the second state; and in the second state, suctioning an object from around an opening of the suction pipeline toward the opening of the suction pipeline and into an interior of the suction pipeline.

17. The method according to claim 16, wherein applying pressure includes supplying a fluid to the interior of the suction pipeline.

18. The method according to claim 16, further comprising:

attaching the suction pipeline on the outer peripheral surface of the insertion portion, wherein the insertion portion is part of an endoscope.

19. The method according to claim 18, wherein attaching the suction pipeline on the outer peripheral surface of the insertion portion includes attaching by bonding.

* * * * *